United States Patent [19]

Heath et al.

[11] Patent Number: 5,705,655
[45] Date of Patent: Jan. 6, 1998

[54] AMPHIPHILIC NITROGEN CONTAINING IMIDAZOLINIUM DERIVATIVE COMPOUNDS AND USES

[75] Inventors: Timothy D. Heath; Igor Solodin, both of Madison, Wis.

[73] Assignee: Megabios Corporation, Burlingame, Calif.

[21] Appl. No.: 247,963

[22] Filed: May 24, 1994

Related U.S. Application Data

[63] Continuation-in-part of Ser. No. 157,727, Nov. 24, 1993, abandoned, which is a continuation-in-part of Ser. No. 991,935, Dec. 17, 1992, abandoned.

[51] Int. Cl.$^6$ ................ C07D 233/14; C07D 233/22; A61K 31/415
[52] U.S. Cl. ........................ 548/350.1; 514/400
[58] Field of Search ................ 548/850.1; 514/400

[56] References Cited

U.S. PATENT DOCUMENTS

| | | | |
|---|---|---|---|
| 2,945,821 | 7/1960 | Sterlin | 548/350.1 X |
| 3,186,912 | 6/1965 | Beamer | 548/350.1 X |
| 3,205,092 | 9/1965 | Rosenberg | 548/350.1 X |
| 3,210,312 | 10/1965 | Rosenberg et al. | 548/350.1 X |
| 3,216,957 | 11/1965 | Krumm | 548/350.1 X |
| 3,313,825 | 4/1967 | Rosenberg et al. | 548/350.1 |
| 5,264,618 | 11/1993 | Felgner et al. | 560/224 |

OTHER PUBLICATIONS

Brigham et al. (1989) "Rapid Communication: In Vivo Transfection of Murine Lungs with a Functioning Prokaryotic Gene using a Liposome Vehicle" *Am. J. Med. Sci.*, 298:278–281.
Hazinski et al. (1991) "Localization and Induced Expression of Fusion Genes in the Rat Lung" *Am. J. Resp. Cell Molec. Biol.*, 4:206–209.
Wu and Wu (1988) "Receptor–mediated Gene Delivery and Expression In Vivo" *J. Biol. Chem.*, 263:14621–14624.
Stribling et al. (1992) "Aerosol Gene Delivery In Vivo" *Proc. Natl. Acad. Sci. (USA)* 89:11277–11281.
Yoshimura et al. (1992) "Expression of the Human Cystic Fibrosis Transmembrane Conductance Regulator Gene in the Mouse Lung" *Nucleic Acids Research*, 20:3233–3240.
Malone et al. (1989) "Cationic Liposome–mediated RNA Transfection" *Proc. Natl. Acad. Sci. (USA)*, 86:6077–6081.
Debs et al. (1990) "Regulation of Gene Expression In Vivo by Liposome–mediated Delivery of a Purified Transcription Factor" *J. Biol. Chem.*, 265:10189–10192.
Nabel et al. (1990) "Site–Specific Gene Expression In Vivo by Direct Gene Transfer into the Arterial Wall" *Science*, 249:1285–1288.
Wolff et al. (1990) "Direct Gene Transfer into Mouse Muscle In Vivo" *Science*, 247:1465–1468.
Wang and Huang (1987) "pH–Sensitive Immunoliposomes Mediate Target–Cell–Specific Delivery and Controlled Expression of Foreign Gene in Mouse" *Proc. Natl. Acad. Sci. (USA)*, 84:7851–7855.
Felgner et al. (1987) "Lipofection: A Highly Efficienct, Lipid–mediated DNA–transfection Procedure" *Proc. Natl. Acad. Sci. (USA)*, 84:7413–7416.
Friedmann (1989) "Progress Toward Human Gene Therapy" *Science* 244:1275–1281.
Rosenfeld et al. I (1992) "In Vivo Transfer of the Human Cystic Fibrosis Transmembrane Conductance Regulator Gene to the Airway Epiethelium" *Cell* 58:143–155.
Rosenfeld et al. II (1991) "Adenovirus–Mediated Transfer of a Recombinant α1–Antitrypsin Gene to the Lung Epithelium in Vivo" *Science* 252:431–434.
Ferm et al., (1954) "*Chem. Rev.*" 54:593–613.
Glankler et al., *J. Am. Oil Chemists'Soc.*, Nov. (1979) 56:802A–805A.
Mat K. Schwitzer (6 Jan. 1979) *Chemistry and Industry*, pp. 11–15.
Chitwood et al., (Dec., 1935) *J. Am. Chem. Soc.* 57,:2424–2427.
J.L. Riebsomer (Apr., 1948) *J. Am. chem. Soc.* 70:1629–1632.
Butler et al. I (1976) *J. Chem. Soc. Perkin Trans. I*, pp. 386–389.
Butler et al. II (1978) *J. Chem. Soc. Perkin Trans. I*, pp. 373–377.
Butler et al. III (1983) *J. Chem. Soc. Perkin Trans. I*, pp. 2197–2200.
Perillo et al. (Aug., 1970) *J. Heterocycl. Chem.* 7:791–798.
Hill et al. (Apr., 1939) *J. Am. Chem. Soc.* 61:822–825.
Canonico et al., abstract (4 May 1991) *Clinical Research* 39:2:219A.
Samuel R. Aspinall (Nov., 1939) *J. Am. Chem. Soc.* 61:3195–3197.

*Primary Examiner*—Floyd D. Higel
*Attorney, Agent, or Firm*—McDonnell Boehnen Hulbert & Berghoff

[57] ABSTRACT

Amphiphiles containing an imidazdinium ring system are provided that are non-toxic to the host mammal. The amphiphiles are used to produce liposomes useful as carriers for delivering macromolecules intracellularly.

11 Claims, No Drawings

AMPHIPHILIC NITROGEN CONTAINING IMIDAZOLINIUM DERIVATIVE COMPOUNDS AND USES

CROSS-REFERENCE TO RELATED APPLICATIONS

This application is a continuation-in-part of U.S. Ser. No. 08/157,727, filed Nov. 24, 1993, now abandoned, which is a continuation-in-part of U.S. Ser. No. 07/991,935, filed Dec. 17, 1992, now abandoned, which disclosures are herein incorporated by reference.

FIELD OF THE INVENTION

This invention relates to nitrogen-containing amphiphiles and their use in the preparation of liposomes and other lipid-containing carriers of pharmaceutical substances, including nucleic acids used in gene therapy.

BACKGROUND OF THE INVENTION

Liposomes are one of a number of lipid-based materials used as biological carriers and have been used effectively as carriers in a number of pharmaceutical and other biological situations, particularly to introduce drugs, radiotherapeutic agents, enzymes, viruses, transcriptional factors and other cellular vectors into a variety of cultured cell lines and animals. Successful clinical trials have examined the effectiveness of liposome-mediated drug delivery for targeting liposome-entrapped drugs to specific tissues and specific cell types. See, for example, U.S. Pat. No. 5,264,618, which describes a number of techniques for using lipid carriers, including the preparation of liposomes and pharmaceutical compositions and the use of such compositions in clinical situations. However, while the basic methodology for using liposome-mediated vectors is well developed, improvements in the materials used in the methods, both in terms of biocompatibility and in terms of effectiveness of the carrier process, are still desirable.

In particular, the expression of exogenous genes in humans and/or various commercially important animals will ultimately permit the prevention and/or cure of many important human diseases and the development of animals with commercially important characteristics. Genes are high molecular weight, polyanionic molecules for which carrier-mediated delivery usually is required for DNA transfection of cells either in vitro or in vivo. Therefore it is of interest to develop lipid transfection vectors which will enhance both the delivery and the ultimate expression of the cloned gene in a tissue or cell of interest. Since in some instances a treatment regimen will involve repeated administration of a gene (or other pharmaceutical product), it also is of interest that the lipid carriers be nontoxic to the host, even after repeated administration.

RELEVANT LITERATURE

Literature describing the use of liposomes as carriers for DNA include the following: (Friedmann (1989), supra; Brigham, et al., (1989) Am. J. Med. Sci., 298:278–281; Nabel, et al. (1990) Science, 249:1285–1288; Hazinski, et al. (1991) Am. J. Resp. Cell Molec. Biol., 4:206–209; and Wang and Huang (1987) Proc. Natl. Acad. Sci. (USA), 84:7851–7855); coupled to ligand-specific, cation-based transport systems (Wu and Wu (1988) J. Biol. Chem., 263:14621–14624) or the use of naked DNA expression vectors (Nabel et al. (1990), supra; Wolff et al. (1990) Science, 247:1465–1468). Direct injection of transgenic material into tissue produced only localized expression (Rosenreid (1992) supra); Rosenfeld et at. (1991) supra). Brigham et al. (1989) supra; Nabel (1990) supra; and Hazinski et at. (1991) supra). The Brigham et at. group (Am. J. Med. Sci. (1989) 298:278–281 and Clinical Research (1991) 39 (abstract) have reported in vivo transfection restricted to lungs of mice following either intravenous or intratracheal administration of a DNA liposome complex. See also Stribling et at. Proc. Natl. Acad. Sci. (USA) 89:11277–11281 (1992) which reports the use of liposomes as carriers for aerosol delivery of transgenes to the lungs of mice and Yoshimura et at. Nucleic Acids Research (1992) 20:3233–3240.

Cationic lipid carriers have been shown to mediate intracellular delivery of plasmid DNA (Felgner, et at., Proc. Natl. Acad. Sci. USA (1987) 84:7413–7416); mRNA (Malone, et at., Proc. Natl. Acad. Sci. USA (1989) 86:6077–6081); and purified transcription factors (Debs, et at., J. Biol. Chem. (1990) 265:10189–10192), in functional form.

SUMMARY OF THE INVENTION

Biodegradable, novel, amphiphilic imidazolinium derivatives are provided as are the methods of their use. The cationic amphiphiles are capable of forming complexes with nucleic acids, and other biological compounds and the nucleic acid complexes are capable of transforming mammalian cells. The amphiphiles of the invention yield nontoxic degradation products when subjected to endogenous enzymatic processes.

DESCRIPTION OF SPECIFIC EMBODIMENTS

Metabolizable amphiphilic imidazolinium derivatives are provided which are useful as carriers for biologically active molecules, such as antibiotics or nucleic acids used in cell transformation processes. The use of the amphiphilic materials as nucleic acid carriers is described in detail, since the compositions prepared using the amphiphiles are particularly efficacious for this purpose. However, the amphiphiles are also useful in standard drug delivery regimens, such as for the delivery of antibiotics to the lungs of a patient.

It will be apparent that the cations of the invention must be present in association with one or more anions, e.g., hydroxide, chloride, or bromide ions or more complex organic anions or bases. The synthetic technique that is described below for producing these amphiphiles initially creates a hydroxide salt of the cationic amphiphile. However, the particular anion associated with an amphiphilic cation is not critical to the formation or utility of the amphiphilic cation and may exchange (in whole or part) for other anions during use of the composition. Alternatively, the anion can be deliberately exchanged, such as by dissolving the initially formed salt (or an intermediate salt) in the presence of an excess of a salt containing the desired anion. Accordingly, the amphiphilic compounds of the invention are described in this specification generally in terms of the cation without reference to any particular anion. A number of specific examples of anions are given, as well as general guidance for selection of anions. For human administration, chloride is the preferred anion; also acceptable are bromide or other physiologically acceptable anions including acetate, succinate and citrate. The cations are either nontoxic themselves, and/or they yield by-products, for example, enzymatic cleavage products, which are nontoxic to a host organism or which are endogenous to a host organism. Generally, both the original lipids and their degradation products are nontoxic to a host organism.

The invention particularly relates to nitrogen-containing amphiphilic cations having the formula:

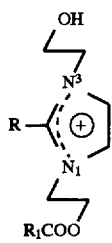

wherein each of R and $R_1$ independently is a straight-chain, aliphatic hydrocarbyl group of 11 to 29 carbon atoms inclusive. Preferred are those cations wherein each of R and $R_1$ independently has from 13 to 23 carbon atoms inclusive. The R and $R_1$ groups are saturated or are unsaturated having one or more ethylenically unsaturated linkages and are suitably the same or are different from each other. Illustrative $R_1$ groups together with the —CO— group to which it is attached (i.e., $R_1$—CO—) include lauroyl, myristoyl, palmitoyl, stearoyl, linoleoyl, eicosanoyl, tricosanoyl and nonacosanoyl (derived from the fatty acids of the corresponding name: lauric, myristic, etc.). When given system names for the $R_1$ groups alone, the corresdonding names of the hydrocarbyl group derived from laurie acid is undecyl; from myristic acid, tridecyl; from palmitic acid, pentadecyl; from stearic acid, heptadecyl; from linoleic acid, cis,cis-8,11-heptadecydienyl; from eicosanoic acid, nonadecyl; from tricosanoic acid, dicosanyl; and from triacontanoic acid, nonacosanyl. Illustrative R groups are indentical to the listed $R_1$ groups, as they are generally derived from the same fatty acids. Illustrative of a cation is 1-[9-(Z)-octadecenoyloxyethyl]-2-[8-(Z)-heptadecenyl]-3-hydroxyethylimidazolinium. Other illustrative cations of the above formula I will be apparent from the formula and the different permutations of above meanings of R and $R_1$.

The compounds of the invention can be synthesized by a rearrangement reaction that is newly discovered, which leads from N,N-bis(2-hydroxyethyl)ethylenediamine through an amino-protected diacylated intermediate to the desired product. The method in general involves synthesizing an imidazolinium ion by heating a precursor compound of formula

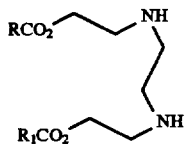

in an organic solvent at a temperature above the boiling point of water, wherein each of R and $R_1$ independently represents an organic group such that the precursor compound is soluble in the solvent and the R and $R_1$ are stable against reaction in the solvent at the temperature. The general synthetic method (including some non-essential steps directed to preferred embodiments and preliminary reactions prior to the key step) is shown in the following reaction scheme:

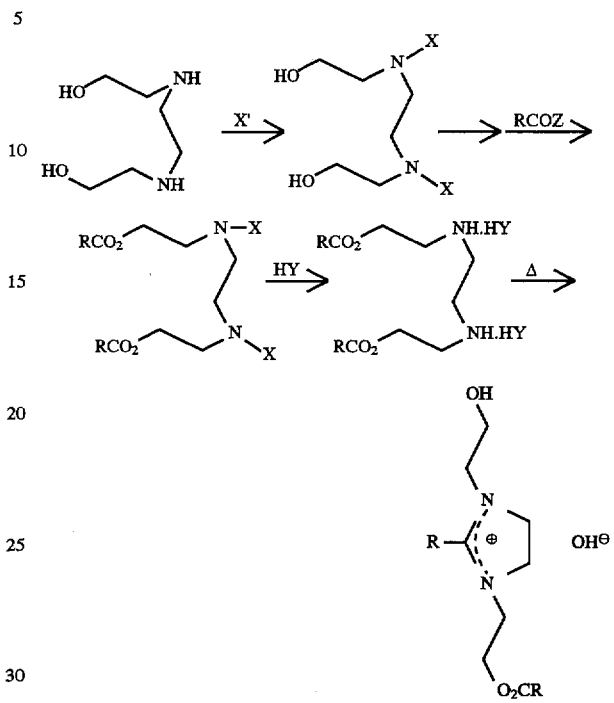

In this reaction scheme, X is any amino protective group that reacts preferably with and protects a secondary amino group in the presence of a hydroxyl group, preferably one which is removable by acid hydrolysis (e.g., with a strong acid such as HCl); X' is the precursor of the X protective group (e.g., an anhydride or acid chloride where the protective group is an acyl group); RCOZ is an acid halide or anhydride in which R is the same R (or $R_1$) that has been previously defined; and HY is a strong acid (e.g., sulfuric acid or one of its derivatives or a hydrogen halide). A preferred amino protecting groups is t-butyloxycarbonyl (from di-t-butyl-pyrocarbonate). Preferred acylating groups are acid chlorides of the fatty acids previously named and described. A preferred acid for the deprotection and rearrangement steps (which can be combined in a single step) is HCl. Heat for the rearrangement reaction is preferably provided by reflux in a solvent having a boiling point in the range 100° to 200°, preferably 100° to 150° C. The initial imidazolinium ion is formed as a hydroxide salt and/or chloride salt (if prepared using HCl as the acid), but the anion (counter ion) can be replaced by exchange as previously described.

This newly discovered rearrangement reaction and the ensuing overall synthesis need not be restricted to production of the specified cationic amphiphiles. It represents a general synthesis of imidizolium compounds of the formula

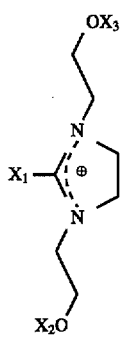

in which $X_1$ represents the residue of an acyl group after the rearrangement reaction as shown (from H to a complex organic group) while $X_2$ and $X_3$ independently represent H or an organic group. $X_2$ would initially represent R—CO—, but this group could be removed or be replaced by a different organic group using standard chemical reactions; since one of the two potential hydroxyl groups in the initial product is already protected, synthesis of compounds in which $X_2$ and $X_3$ represent different groups can readily be accomplished. Ions in which both $X_2$ and $X_3$ represent H are preferred, as these can be used in the synthesis of numerous imidazolinium compounds. Although there is no particular limit on the structure of the three "X" groups in the general synthesis other than those imposed by solubility or reactivity under the heating conditions being used for the reaction (which will be readily apparent), preferred organic groups are hydrocarbyl groups containing 30 or fewer carbons and their oxygenated products (especially fatty acids and their reaction products as previously described, as well as other hydrocarbyl groups and oxygenated products containing 15 or fewer carbon atoms, preferably 10 or fewer, more preferably hydrocarbyl groups containing no more than one phenyl ring with the remainder of the hydrocarbyl group being composed of alkyl groups, especially alkyl groups of 5 or fewer carbons). Organic groups formed from oxygenated hydrocarbyl groups are preferably carboxylic acids, alcohols, esters, ethers, ketones and aldehydes containing no more than one such functional group per organic group. Examples of imidazolinium ions that can be prepared by the synthesis as described above (with further modification of the hydroxyl groups using simple organic reactions) include 1,3-dihydroxyethylimidazolinium, 1-methoxyethyl-3-hydroxyethylimidazolinium, 1-hydroxyethyl-2-phenyl-3-methylcarboxyethylimidazolinium, 1,3-dimethoxyethoxyethylimidazolinium, 1,3-hydroxyethyl-2-tridecylimidazolinium, and 1-hydroxyethyl-2-cis,cis-8,11-heptadecyldienyl-3-oleoyloxyethylimidazolinium.

Since the reaction is a simple self condensation reaction with the elimination of water, the solvent and/or other reaction conditions are not important to the overall reaction. Any solvent can be used that will dissolve the precursor compound and that has a boiling point above that of water (under the pressure conditions of the reaction, which are not limiting). If an acid catalyst is used to speed up the reaction, a protic solvent is preferred in order to provide easier proton exchange. Ethylene glycol and other alcohols having a boiling point above 100° C. are preferred.

The cationic lipids of the invention are typically used as carriers for various biological molecules, such as antibiotics or nucleic acids. In particular, the cationic lipids can be used alone or combined with other lipids in formulations for the preparation of lipid vesicles or liposomes for use in intracellular delivery systems. Uses contemplated for the lipids of the invention include transfection procedures corresponding to those presently known that use amphiphilic lipids, including those using commercial cationic lipid preparations, such as Lipofectin ™, and various other published techniques using conventional cationic lipid technology and methods. The cationic lipids of the invention can be used in pharmaceutical formulations to deliver therapeutic agents by various routes and to various sites in an animal body to achieve a desired therapeutic effect. When considering cell transfection as the intended use, it has been determined that the free hydroxyl group of the imidizolinium ion should not be acylated with an additional fatty acid groups, as such "tri fatty acid" have been found not to be effective in transforming cells.

Because such techniques are generally known in the art, background information and basic techniques for the preparation of pharmaceutical compositions containing lipids will not be repeated at this time. A reader unfamiliar with this background information is referred to the publications under the heading Relevant Literature above and further to U.S. Pat. No. 5,264,618. This last-cited patent describes a number of therapeutic formulations and methods in detail, including examples of the use of specific cationic lipids (different from those described here) that can be followed in detail by substituting the cationic lipids of the present invention for those described in the patent. Compositions of the present invention will minimally be useable in the manner described in the patent, although operating parameters may need to be modified in order to achieve optimum results, using the specific information provided for compounds of the invention in this specification along with the knowledge of a person skilled in the arts of lipid preparation and use.

The lipids of the present invention have been shown to be particularly useful and advantageous in the transfection of animal cells by genetic material. Additionally, since these compositions are degraded by enzymatic reactions in animal cells to components that are typically endogenous to the cells, the compositions provide a number of advantages in the area of low toxicity when compared to same previously known cationic lipids. These and other advantages of the invention are discussed in detail below. The remainder of this discussion is directed principally to selection, production, and use parameters for the cationic lipids of the present invention that may not immediately be apparent to one of ordinary skill in the art.

Particularly where it is desirable to target a lipid-DNA complex to a particular cell or tissue, a lipid mixture used as a carrier can be modified in a variety of ways. By a lipid mixture is intended a formulation prepared from the cationic amphiphile of the invention, with or without additional agents such as steroids, and includes liposomes, interleaved bilayers of lipid, and the like. Steroids, e.g. cholesterol or ergosterol, can be used in combination with the cationic amphiphiles when used to prepare mixtures. In some embodiments, the lipid mixture will have from 0–67 mole percent steroid, preferably about 33 to 50 mole percent steroid. A lipid-DNA complex is the composition obtained following combination of DNA and a lipid mixture. Non-lipid material (such as biological molecules being delivered to an animal or plant cell or target-specific moieties) can be conjugated through a linking group to one or more hydrophobic groups, e.g. using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains, which will allow for their association with the lipid mixture without covalent linking to one or more lipid groups.

For the most part, the active compounds to be bound to the lipid mixture are ligands or receptors capable of binding to some biological molecule of interest that is present in the target cell. A ligand can be any compound of interest which can specifically bind to another compound, referred to as a receptor, the ligand and receptor forming a complementary pair. The active compounds bound to the lipid mixture can vary widely, from small haptens (molecular weights of about 125 to 2,000) to antigens which will generally have molecular weights of at least about 6,000 and generally less than about 1 million, more usually less than about 300,000. Of particular interest are proteinaceous ligands and receptors that have specific complementary binding partners on cell surfaces. Illustrative active compounds include chorionic gonadotropin, encephalon, endorphin, luteinizing hormone, morphine, epinephrine, interferon, ACTH, and polyiodothyronines and fragments of such compounds that retain the ability to bind to the same cell-surface binding partners that bind the original (non-fragment) molecules.

The number of targeting molecules (either ligand or receptor) bound to a lipid mixture will vary with the size of the liposome, the size of the molecule, the binding affinity of the molecule to the target cell receptor or ligand, and the like. Usually, the bound active molecules will be present in the lipid mixture in from about 0.05 to 2 mole percent, more usually from about 0.01 to 1 mole percent based on the percent of bound molecules to the total number of molecules available in the mixture for binding.

The surface membrane proteins which bind to specific effector molecules (usually soluble molecules in the external environment of the cell) are referred to as receptors. In the present context, receptors include antibodies and immunoglobulins since these molecules are found on the surface of certain cells. However, since antibodies are generally used to bind liposomes to receptor molecules on target cells, the antibodies and immunoglobulins bound to a liposome containing a cationic lipid of the invention can also be considered to be ligands. The immunoglobulins may be monoclonal or polyclonal, preferably monoclonal. Usually the immunoglobulins will be IgG and IgM, although the other immunoglobulins may also find use, such as IgA, IgD, and IgE. The intact immunoglobulins may be used or only fragments thereof, such as Fab, F(ab')$_2$F$_r$, or F$_v$, fragments as well as a complete light or heavy chain.

For antibodies used as cell-targeting ligands, antibodies of interest are those that bind to surface membrane antigens such as those antigens comprising the major histocompatibility complex, particularly the HLA-A, -B, -C and -D. Other surface antigens include thy-1, leu-5, and Ia.

The cationic amphiphiles are particularly useful as carriers for anionic compounds, particularly polyanionic macromolecules such as nucleic acids. Where the amphiphiles are intended for use in vivo, particularly in vivo in humans, or where it is necessary to use the amphiphiles repeatedly, it is important to screen the carriers for those which are metabolized to non-toxic by-products and which themselves are not toxic or those which are eliminated from the body without degradation. The elimination of such amphiphilic cations from tissues can be demonstrated in animal experiments. One or more doses of material containing between 0.5 and 10 pmole of the lipid to be tested, complexed with an active component (such as DNA) if desired can be administered to an animal, such as a mouse. At various times after administration, the animals are sacrificed, tissues taken, total lipids extracted using an appropriate solvent extraction system, and the total lipid analyzed for the particular cationic lipid or its partial degradation product using, for example, HPLC.

The cationic amphiphiles are positively charged, and a tight charge complex can be formed between a cationic lipid carrier and a polyanionic nucleic acid, resulting in a lipid carrier-nucleic acid complex which can be used directly for systemic delivery to a mammal or mammalian cell. Where delivery is via aerosolization, the charge complex will withstand both the forces of nebulization and the environment within the lung airways and be capable of transfecting lung cells after the aerosolized DNA:lipid carrier complex has been deposited in the lung following intranasal or intraoral delivery of the aerosolized complex.

To evaluate the efficacy of a particular amphiphilic cation for use as a nucleic acid carrier in an aerosolization process, as well as to determine the optimum concentrations of lipid carrier-nucleic acid complexes, involves a two-step process. The first step is to identify lipid carriers and the concentration of lipid carrier-nucleic acid complexes that do not aggregate when the components are combined or during the significant agitation of the mixture that occurs during the nebulization step. The second step is to identify among those lipids that do not aggregate those complexes that provide for a high level of transfection and transcription of a gene of interest in target cells in the lung. These techniques are described in WO/US PCT/US92/11008 filed Dec. 17, 1992, which disclosure is hereby incorporated by reference.

As an example, a reporter gene CAT (which encodes chloramphenicol acetyltransferase) can be inserted in an expression cassette and used to evaluate each lipid carrier composition of interest. The DNA:lipid carrier complexes are mixed in solutions which do not themselves induce aggregation of the DNA:lipid carrier complexes, such as sterile water. The expression cassette (DNA) is mixed together with each of the lipid carriers to be tested in multiple different ratios, ranging as an example from 4:1 to 1:10 (micrograms of DNA to nanomoles of cationic lipid or total lipid, if a lipid mixture is present). Examination of the stability of the resulting mixtures provides information concerning which ratios result in aggregation of the DNA:lipid carrier complexes and are therefore not useful for use in vivo, and which complexes remain in a form suitable for aerosolization. The ratios which do not result in aggregation are tested in animal models to determine which of the DNA:lipid carrier ratios confer the highest level of transgene expression in vivo. For example, for aerosol-based transfection, the optimal DNA:lipid carrier ratios for lipid mixtures such as N-[1-(2,3-dioleyloxy)propyl]-N,N,N-triethylammonium chloride(DOTMA):dioleoylphosphatidylethanolamine(DOPE) (the components of this mixture being present in a 1:1 weight ratio) and dimethyl dioctadecyl ammonium bromide (DDAB):Chol (1:1) are 1 to 1.

If the cationic amphiphile is used for injection, then it need be evaluated only for whether it is effective for transfection of a target cell. For 1-[9-(Z)octadecenoyloxyethyl]-2-[8-(Z)-heptadecenyl]-3-hydroxyethylimidazolinium in a 1:1 weight ratio with cholesterol, the DNA:lipid carrier ratio is preferably in the range of from 1:2 to 1:7 (microgram DNA:nanomoles cationic lipid).

Particular cells can be targeted by the use of particular cationic lipids for preparation of the lipid-mixture carriers, for example, by the use of E-DMPC to target lung cells preferentially, or by modifying the amphiphiles to direct them to particular types of cells using site-directing molecules. Thus antibodies or ligands for particular receptors may be employed, to target a cell associated with a particular surface protein. A particular ligand or antibody can be conjugated to the cationic amphiphile in accordance with conventional techniques, either by conjugating the site-directing molecule to a lipid for incorporation into the lipid bilayer or by providing a linking group on a lipid present in the bilayer for linking to a functionality of the site-directing compound. Such techniques are well known to those skilled in the art.

The various lipid carrier-nucleic acid complexes wherein the lipid carrier is a liposome are prepared using methods well known in the art. Mixing conditions can be optimized by visual examination of the resultant lipid-DNA mixture to establish that no precipitation occurs. To make the lipid-DNA complexes more visible, the complexes can be stained with a dye which does not itself cause aggregation, but which will stain either the DNA or the lipid. For example, Sudan black (which stains lipid) can be used as an aid to examine the lipid-DNA mixture to determine if aggregation has occurred. Particle size also can be studied with methods known in the art, including electron microscopy, laser light scattering, Coulter™ counting/sizing, and the like. Standard-size beads can be included as markers for determining the size of any liposomes or aggregates that form. By "lipid carrier-nucleic acid complex" is meant a nucleic acid sequence as described above, generally bound to the surface of a lipid carrier preparation, as discussed below. The lipid carrier preparation can also include other substances, such as enzymes necessary for integration, transcription and translation or cofactors. Furthermore, the lipid carrier-nucleic acid complex can include targeting agents to deliver the complex to particular cell or tissue types. Generally, the nucleic acid material is added to a suspension of preformed liposomes which may be multi-lamellar vesicles (MLVs) or small unilamellar vesicles (SUVs), usually SUVs formed by sonication. The liposomes themselves are prepared from a dried lipid film that is resuspended in an appropriate mixing solution such as sterile water or an isotonic buffer solution such as 10 mM Tris/NaCl or 5 % dextrose in sterile water and sonicated to form the liposomes. Then the preformed lipid carriers are mixed directly with the DNA.

Mixing and preparing of the lipid-DNA complex can be critically affected by the sequence in which the lipid and DNA are combined. Generally, it is preferable (to minimize aggregation) to add the lipid to the DNA at ratios of DNA:lipid of up to 1:2 inclusive (microgram DNA:nanomoles cationic lipid). Where the ratio of DNA:lipid is 1:4 or higher, better results are generally obtained by adding the DNA to the lipid. In either case, mixing should be rapidly achieved by shaking or vortexing for small volumes and by use of rapid mixing systems for large volumes. The lipid carrier and DNA form a very stable complex due to binding of the negatively charged DNA to the cationic lipid carriers. SUVs find use with small nucleic acid fragments as well as with large regions of DNA ($\geq$250 kb).

In preparing the lipid carrier-nucleic acid complex for nebulization, care should be taken to exclude any compounds from the mixing solution which promote the formation of aggregates of the lipid carrier-nucleic acid complexes. Large particles generally will not be aerosolized by the nebulizer, and even if aerosolized would be too large to penetrate beyond the large airways. Aggregation of the lipid carrier-nucleic acid complex is prevented by controlling the ratio of DNA to lipid carrier, minimizing the overall concentration of DNA:lipid carrier complex in solution, usually less than 5 mg DNA/8 ml solution, and avoiding the use of chelating agents such as EDTA and/or significant amounts of salt, either of which tends to promote macro-aggregation. The preferred excipient is water, dextrose/water or another solution having low or zero ionic strength. Further, the volume should be adjusted to the minimum necessary for deposition in the lungs of the host mammal, while at the same time taking care not to make the solution too concentrated so that aggregates form. Increasing the volume of the solution is to be avoided if possible due to the need to increase the inhalation time for the host animal to accommodate the increased volume. In some cases, it may be preferable to lyophilize the lipid carrier-nucleic acid complexes for inhalation. Such materials are prepared as complexes as described above, except that a cryoprotectant such as mannitol or trehalose is included in the buffer solution which is used for preparation of the lipid carrier-DNA complexes. Any glucose generally included in such a buffer is preferably omitted. The lipid carrier complex is rapidly freeze-dried following mixing of the lipid and DNA. The mixture can be reconstituted with sterile water to yield a composition which is ready for administration to a host animal.

Where the amphiphiles form liposomes, the liposomes may be sized in accordance with conventional techniques, depending upon the desired size. In some instances, a large liposome injected into the bloodstream of an animal has higher affinity for lung cells as compared to liver cells. Therefore, the particular size range may be evaluated in accordance with any intended target tissue by administering lipid-nucleic acid complexes of varying particle sizes to a host animal and determining the size of particle which provides the desired results.

The cationic amphiphiles complexed with nucleic acid of this invention can be administered in a variety of ways to a host, such as intravenously, intramuscularly, subcutaneously, transdermally, topically, intraperitoneally, intravascularly, by aerosol, following nebulization, and the like. Normally, the amphiphiles will be injected in solution where the concentration of compound bound to or entrapped in the liposome will dictate the amount to be administered. This amount will vary with the effectiveness of the compound being administered, the required concentration for the desired effect, the number of administrations, and the like. In some instances, particularly for aerosol administration, the lipid-DNA complexes can be administered in the form of a lyophilized powder.

Upon administration of the amphiphiles, when a targeting moiety is used, the amphiphiles preferentially bind to a cell surface factor complementary to the compounds bound to the liposome. If no targeting moiety is bound to the liposome, then it binds to cell surface by lipophilic interactions. The liposome normally are transferred into the cell by endocytosis.

The cationic amphiphiles find use for complexing with nucleic acid or protein for transporting these macromolecules in vivo. The nucleic acid can include DNA, RNA, antisense RNA or other antisense molecules. Cationic amphiphiles that form liposomes also find use in drug delivery, where the drug can be entrapped within the liposome or bound to the outside.

The following examples are offered by way of illustration and not by way of limitation.

EXAMPLES

Example 1

Synthesis of 1-Acyloxyethyl-2-alkyl(alkenyl)-3-hydroxyethylimidazolinium derivatives Commercially available N,N-bis(2-hydroxyethyl) ethylenediamine was N,N-diprotected using di-tert-butylpyrocarbonate, then O,O-diacylated using an appropriate acyl chloride. N-BOC protection groups were cleaved with 4M HCl in dioxane, and the resulting hydrochloride salt was subjected to thermal rearrangement in a suitable high boiling solvent to afford 1-acyloxyethyl-2-alkyl(alkenyl)-3-hydroxyethylimidazolinium derivatives:

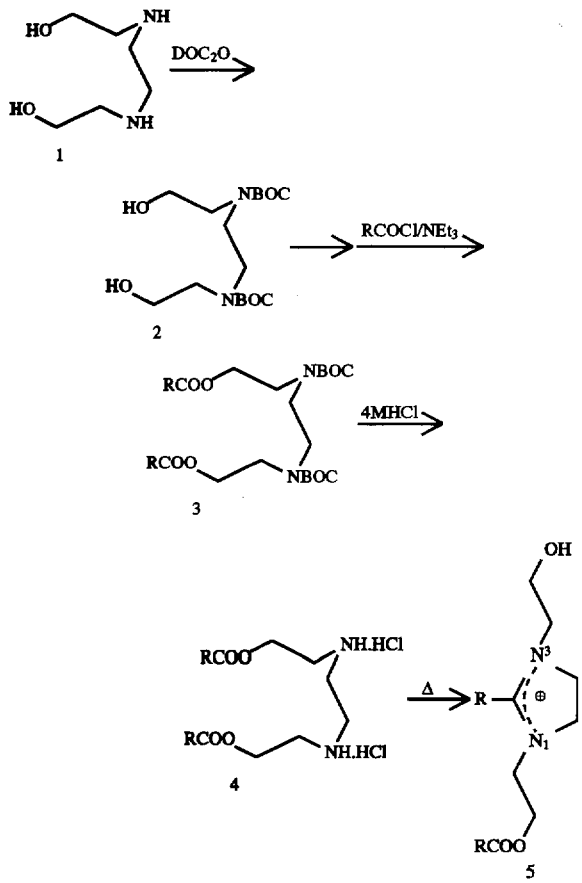

Example: (a) Synthesis of 1-[9-(Z)-octadecanoyloxyethyl]-2-[8-(Z)-heptadecenyl]-3-hydroxyethylimidazolinium hydroxide.
N,N'-Di-BOC-diamine (2.)

To a solution of 1.48 g (0.01 mol) of N,N'-bis(2-hydroxyethyl)ethylenediamine 1 in 100 ml. of CHCl$_3$ were added 4.57 g (0.021 mol) of di-tert-butyl pyrocarbonate and 5 ml of sat. aq. NaHCO$_3$. The mixture was stirred at room temperature for 5 hrs, then the organic layer was separated, washed with water (25 ml×2), dried over MgSO$_4$, and evaporated on rotavapor. The white crystals obtained were washed with hexane (25 ml×2) and dried under vacuum to get 2.8 g (80%) of product.
N,N'-Di-BOC ester (3.)

To a solution of 0.5 g (0.0014 mol) of 2 in 100 ml of dichloromethane at 0° C. were added 0.7 ml (0.005 mol) of triethylamine, and then 1.2 ml (0.0037 mol) of oleoyl chloride were added in 10 min with stirring. The mixture was stirred at 0° C. for 30 min, and then at room temperature for 45 min. The resulting solution was washed with 10% citric acid (50 ml×2), with 10% aqueous solution of sodium bicarbonate (50 ml×2), dried over MgSO$_4$, filtered, filtrate evaporated on rotavapor and the residue was chromatographed on silica gel using 0–15% EtOAc/Hexane to get 1.2 g (94%) of N,N'-Di-BOC ester 3.

Diamino ester (4.)

To 1.2 g (0.00136 mol) of N,N'-Di-BOC ester 3 were added 12 ml of 4M solution of HCl in dioxane and the mixture was stirred at room temperature for 2 hrs. The resulting suspension was evaporated on rotavapor, diluted with ether (20 ml), faltered, washed with ether (15 ml×2) and dried in vacuum to get 1.07 g (100%) of diamino ester 4.

1-[9-(Z)-octadecenoyloxyethyl]-2-[8-(Z)-heptadecenyl]-3-hydroxyethylimidazolinium hydroxide (5.)

To a mixture of 1.16 g (0.00149 mol) of diamino ester 4 were added 3 ml of ethylene glycol and the mixture was stirred at 110° C. (oil bath) for 30 min. The solution obtained was dissolved in 150 ml of CHCl$_3$ and washed with 5% NaCl (50 ml×3) using MeOH. The organic layer was separated, dried over MgSO$_4$, evaporated on rotavapor and the rest was chromatographed on silica gel using 5–20% MeOH/CHCl$_3$ to get 0.95 g (75%) of product as yellowish oil.

(b) Transfection using liposomes containing 1-[9-(Z) octadecenoyloxyethyl]-2-[8-(Z)-heptadecenyl]-3-hydroxyethylimidazolinium compound 5.

Liposomes containing compound 5 in a 1:1 molar ratio with cholesterol was tested as a DNA carrier for gene transfer and expression in mice. The plasmid used was pZN51. The methods and plasmids used are described in more detail in WO93/24640. The liposomes were in a 10 mM stock in 5% dextrose. The liposome:plasmid DNA ratios were screened for the presence of aggregation. Ratios from 1:2 to 1:7 (µg plasmid DNA to nanomoles cationic lipid) were screened. DNA:liposome ratios that did not produce aggregation were then tested in mice. 100 µg of pZN51 was complexed to 500 nanomoles of DDAB:cholesterol liposomes as a positive control and an uninjected mouse served as the negative control (N).

ICR female mice (25 g) were used for the in vivo studies. A dose of 100 µg plasmid DNA in 0.2 ml 5% dextrose in water was injected by tail vein per mouse.

The lung, heart, liver, kidney and spleen were removed after 24 hours. Each organ was homogenized in 0.3 ml of 0.25M Tris-HCl pH 7.8, 5 mM EDTA, and the resulting extract was centrifuged and then subjected to 3 cycles of freeze-thaw and then treated to 65° C. for 20 min. The protein concentration of lung, heart, liver and kidney extracts were quantitated using a ninhydrin-based protein assay (Bio-Rad, Berkeley, Calif.), and same amount of total protein from each tissue extract was added in the CAT assay, together with 10 µl of 20 mM acetyl CoA+12 µl of $^{14}$C-chloramphenicol (25 µCi/ml, 55 mCi/mmole, Amersham)), at 37° C. for 13 hrs.

The highest levels of CAT activity in the lung, heart, liver, kidney and spleen were produced with liposomes in a 1:6 ratio with DNA. The CAT activities appear to be higher than those produced by DDAB:CHOL in a 1:5 ratio.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A nitrogen-containing amphiphile of the formula:

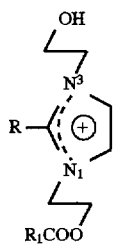

wherein each R and $R_1$ independently is a straight-chain, aliphatic hydrocarbyl group of 11 to 29 carbon atoms inclusive.

2. The amphiphile of claim 1 wherein R independently has from 13 to 23 carbon atoms inclusive.

3. The amphiphile of claim 1 wherein R is heptadecyl or $R_1$ is octadecyl.

4. The amphiphile of claim 1 wherein R is tridecyl or $R_1$ is tetradecyl.

5. The amphiphile of claim 1 wherein R is pentadecyl or $R_1$ is hexadecyl.

6. The amphiphile of claim 1 wherein R is heptadecenyl or $R_1$ is octadecyl.

7. The amphiphile of claim 1 wherein said amphiphile is 1-[9-(Z)-octadecenoyloxyethyl]-2-[8-(Z)-heptadecenyl]-3-hydroxyethylimidazolinium.

8. A method for synthesizing an imidazolinium ion, which comprises:

heating a precursor compound of formula

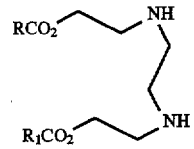

in an organic solvent at a temperature above the boiling point of water, wherein each of R and $R_1$ independently represents an organic group such that said precursor compound is soluble in said solvent and said R and $R_1$ are stable against reaction in said solvent at said temperature.

9. The method of claim 8, wherein said solvent is a protic solvent.

10. The method of claim 8, wherein said heating occurs in the presence of an acid.

11. The method of claim 10, wherein said acid is HCl.

* * * * *